United States Patent
Wang (10) Patent No.: US 10,376,141 B2
(45) Date of Patent: *Aug. 13, 2019

(54) FUNDUS IMAGING SYSTEM

(71) Applicant: Welch Allyn, Inc., Skaneateles Falls, NY (US)

(72) Inventor: Ynjiun Paul Wang, Cupertino, CA (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/872,680

(22) Filed: Jan. 16, 2018

(65) Prior Publication Data

US 2018/0140188 A1 May 24, 2018

Related U.S. Application Data

(63) Continuation of application No. 15/297,073, filed on Oct. 18, 2016, now Pat. No. 9,918,629, which is a
(Continued)

(51) Int. Cl.
*A61B 3/14* (2006.01)
*A61B 3/00* (2006.01)
(Continued)

(52) U.S. Cl.
CPC .............. *A61B 3/12* (2013.01); *A61B 3/0008* (2013.01); *A61B 3/0025* (2013.01); *A61B 3/14* (2013.01); *A61B 3/152* (2013.01)

(58) Field of Classification Search
CPC ........... A61B 3/14; A61B 3/0025; A61B 3/12; A61B 3/102; A61B 3/0058
(Continued)

(56) References Cited

U.S. PATENT DOCUMENTS 5,048,946 A 9/1991 Sklar et al.
5,557,350 A 9/1996 Yano
(Continued)

FOREIGN PATENT DOCUMENTS

CN 102324014 A 1/2012
CN 10262304 A 8/2012
(Continued)

OTHER PUBLICATIONS

Mayer et al., "Wavelet denoising of multiframe optical coherence tomography data," Biomedical Optics Express, vol. 3, No. 3, pp. 572-589 (Mar. 1, 2012).
(Continued)

*Primary Examiner* — Mohammed A Hasan
(74) *Attorney, Agent, or Firm* — Merchant & Gould P.C.

(57) ABSTRACT

A fundus imaging system includes: an image sensor array, where the image sensor array includes monochrome photodiodes and global shutter control, an illumination unit with one or more light-emitting diodes that have one or more dies, a computing system including a processor and memory, one or more lenses, one or more reflective mirrors, and a display. In an example method of use, a clinician positions a patient, initiates a focal adjustment, initiates a retinal imaging process, and the same or a different clinician views the image. In some embodiments, the imaging system is configured to analyze the image and identify detected physical attributes in the image relating to the diagnosis and treatment of diabetic retinopathy.

15 Claims, 5 Drawing Sheets

Related U.S. Application Data continuation of application No. 14/939,601, filed on Nov. 12, 2015, now Pat. No. 9,498,126, which is a continuation of application No. 14/177,568, filed on Feb. 11, 2014, now Pat. No. 9,211,064.

(51) Int. Cl.
 *A61B 3/12* (2006.01)
 *A61B 3/15* (2006.01)

(58) Field of Classification Search
 USPC .......................................................... 351/206
 See application file for complete search history.

(56) References Cited

U.S. PATENT DOCUMENTS

| | | |
|---|---|---|
| 5,599,276 A | 2/1997 | Hauptil et al. |
| 5,703,621 A | 12/1997 | Martin et al. |
| 5,713,047 A | 1/1998 | Kohayakawa |
| 5,776,060 A | 7/1998 | Smith et al. |
| 5,784,148 A | 7/1998 | Heacock |
| 5,943,116 A | 8/1999 | Zeimer |
| 6,000,799 A | 12/1999 | Van de Velde |
| 6,011,585 A | 1/2000 | Anderson |
| 6,120,461 A | 9/2000 | Smyth |
| 6,296,358 B1 | 10/2001 | Cornsweet et al. |
| 6,301,440 B1 | 10/2001 | Bolle et al. |
| 6,307,526 B1 | 10/2001 | Mann |
| 6,309,070 B1 | 10/2001 | Svetliza et al. |
| 6,325,511 B1 | 12/2001 | Mizuochi |
| 6,350,031 B1 | 2/2002 | Lashkari et al. |
| 6,556,853 B1 | 4/2003 | Cabib et al. |
| 6,666,857 B2 | 12/2003 | Smith |
| 7,134,754 B2 | 11/2006 | Kerr et al. |
| 7,264,355 B2 | 9/2007 | Rathjen |
| 7,284,859 B2 | 10/2007 | Ferguson |
| 7,311,400 B2 | 12/2007 | Wakil et al. |
| 7,364,297 B2 | 4/2008 | Goldfain et al. |
| 7,380,938 B2 | 6/2008 | Chmielewski, Jr. et al. |
| 7,387,384 B2 | 6/2008 | Heine et al. |
| 7,404,640 B2 | 7/2008 | Ferguson et al. |
| 7,470,024 B2 | 12/2008 | Chinaglia et al. |
| 7,488,294 B2 | 2/2009 | Torch |
| 7,502,639 B2 | 3/2009 | Kerr |
| 7,568,628 B2 | 8/2009 | Wang et al. |
| 7,611,060 B2 | 11/2009 | Wang et al. |
| 7,621,636 B2 | 11/2009 | Su et al. |
| 7,784,940 B2 | 8/2010 | Goldfain et al. |
| 7,809,160 B2 | 10/2010 | Vertegaal et al. |
| 7,871,164 B2 | 1/2011 | Luther et al. |
| 7,926,945 B2 | 4/2011 | Dick et al. |
| 7,963,653 B1 | 6/2011 | Ellman |
| 7,976,162 B2 | 7/2011 | Flitcroft |
| 8,109,634 B2 | 2/2012 | Gil |
| 8,109,635 B2 | 2/2012 | Allon et al. |
| 8,347,106 B2 | 1/2013 | Tsuria et al. |
| 8,366,270 B2 | 2/2013 | Pujol Ramo et al. |
| 8,388,523 B2 | 3/2013 | Vivenzio et al. |
| 8,444,269 B1 | 5/2013 | Ellman |
| 8,488,895 B2 | 7/2013 | Muller et al. |
| 8,534,837 B2 | 9/2013 | Sayeram et al. |
| 8,577,644 B1 | 11/2013 | Ksondzyk et al. |
| 8,585,203 B2 | 11/2013 | Aikawa et al. |
| 8,620,048 B2 | 12/2013 | Nakano et al. |
| 8,649,008 B2 | 2/2014 | Kashani et al. |
| 8,696,122 B2 | 4/2014 | Hammer et al. |
| 8,714,743 B2 | 5/2014 | Verdooner |
| 8,879,813 B1 | 11/2014 | Solanki et al. |
| 9,211,064 B2 | 12/2015 | Wang |
| 9,237,847 B2 | 1/2016 | Wang |
| 9,498,126 B2 | 11/2016 | Wang |
| 9,757,031 B2 | 9/2017 | Wang et al. |
| 9,918,629 B2 * | 3/2018 | Wang ................... A61B 3/14 |
| 10,136,804 B2 | 11/2018 | Wang et al. |
| 10,154,782 B2 | 12/2018 | Farchione et al. |
| 10,159,409 B2 | 12/2018 | Wang et al. |
| 2002/0101568 A1 | 8/2002 | Eberl et al. |
| 2003/0009155 A1 | 1/2003 | Pawlowski et al. |
| 2003/0071970 A1 | 4/2003 | Donnerhacke et al. |
| 2003/0208125 A1 | 11/2003 | Watkins |
| 2005/0012899 A1 | 1/2005 | Ferguson |
| 2005/0043588 A1 | 2/2005 | Tsai |
| 2005/0110949 A1 | 5/2005 | Goldfain et al. |
| 2005/0254008 A1 | 11/2005 | Ferguson et al. |
| 2006/0113386 A1 | 6/2006 | Olmstead |
| 2006/0119858 A1 | 6/2006 | Knighton et al. |
| 2006/0147095 A1 | 7/2006 | Usher et al. |
| 2006/0202036 A1 | 9/2006 | Wang |
| 2006/0202038 A1 | 9/2006 | Wang et al. |
| 2006/0268231 A1 | 11/2006 | Gil et al. |
| 2007/0030450 A1 | 2/2007 | Liang et al. |
| 2007/0174095 A1 | 7/2007 | Bjornberg et al. |
| 2007/0174152 A1 | 7/2007 | Bjornberg et al. |
| 2007/0188706 A1 | 8/2007 | Pearson |
| 2008/0084538 A1 | 4/2008 | Maeda et al. |
| 2008/0165322 A1 | 7/2008 | Su et al. |
| 2008/0231803 A1 | 9/2008 | Feldon et al. |
| 2008/0316426 A1 | 12/2008 | Shibata et al. |
| 2009/0096885 A1 | 4/2009 | Robinson et al. |
| 2009/0225277 A1 | 9/2009 | Gil |
| 2009/0275929 A1 | 11/2009 | Zickler |
| 2009/0316115 A1 | 12/2009 | Itoh et al. |
| 2009/0323022 A1 * | 12/2009 | Uchida ................... A61B 3/12 |
| | | 351/206 |
| 2009/0323023 A1 | 12/2009 | Kogawa et al. |
| 2010/0007849 A1 | 1/2010 | Liesfeld et al. |
| 2010/0014052 A1 | 1/2010 | Koschmieder et al. |
| 2010/0085538 A1 | 4/2010 | Masaki et al. |
| 2010/0110375 A1 | 5/2010 | Nishio et al. |
| 2010/0149489 A1 | 6/2010 | Kikawa et al. |
| 2010/0208961 A1 | 8/2010 | Zahniser |
| 2010/0238402 A1 | 9/2010 | Itoh et al. |
| 2011/0001927 A1 | 1/2011 | Kasper |
| 2011/0028513 A1 | 2/2011 | Zhuo et al. |
| 2011/0043756 A1 | 2/2011 | Kahn et al. |
| 2011/0169935 A1 | 7/2011 | Henriksen |
| 2011/0234977 A1 | 9/2011 | Verdooner |
| 2011/0242306 A1 | 10/2011 | Bressler et al. |
| 2011/0261184 A1 | 10/2011 | Mason et al. |
| 2011/0299034 A1 | 12/2011 | Walsh et al. |
| 2011/0299036 A1 | 12/2011 | Goldenholz |
| 2012/0002167 A1 | 1/2012 | Kondoh |
| 2012/0044456 A1 | 2/2012 | Hayashi |
| 2012/0050677 A1 | 3/2012 | Ohban |
| 2012/0121158 A1 | 5/2012 | Sekine et al. |
| 2012/0147327 A1 | 6/2012 | Shikaumi et al. |
| 2012/0169995 A1 | 7/2012 | Mohr et al. |
| 2012/0200690 A1 | 8/2012 | Beasley |
| 2012/0213423 A1 | 8/2012 | Xu et al. |
| 2012/0218301 A1 | 8/2012 | Miller |
| 2012/0229617 A1 | 9/2012 | Yates et al. |
| 2012/0229764 A1 | 9/2012 | Tomatsu et al. |
| 2012/0248196 A1 | 10/2012 | Wang |
| 2012/0249956 A1 | 10/2012 | Narasimha-Iyer |
| 2012/0257163 A1 | 10/2012 | Dyer et al. |
| 2012/0281874 A1 | 11/2012 | Lure |
| 2012/0320340 A1 | 12/2012 | Coleman, III |
| 2013/0002711 A1 | 1/2013 | Sakagawa |
| 2013/0010260 A1 | 1/2013 | Tumlinson |
| 2013/0016320 A1 | 1/2013 | Naba |
| 2013/0033593 A1 | 2/2013 | Chinnock et al. |
| 2013/0057828 A1 | 3/2013 | de Smet |
| 2013/0063698 A1 | 3/2013 | Akiba et al. |
| 2013/0128223 A1 | 5/2013 | Wood et al. |
| 2013/0162950 A1 | 6/2013 | Umekawa |
| 2013/0169934 A1 | 7/2013 | Verdooner |
| 2013/0176533 A1 * | 7/2013 | Raffle .................... A61B 3/113 |
| | | 351/209 |
| 2013/0194548 A1 | 8/2013 | Francis et al. |
| 2013/0201449 A1 | 8/2013 | Walsh et al. |
| 2013/0208241 A1 | 8/2013 | Lawson et al. |
| 2013/0211285 A1 | 8/2013 | Fuller et al. |
| 2013/0215387 A1 | 8/2013 | Makihira et al. |
| 2013/0222763 A1 | 8/2013 | Bublitz et al. |

(56) References Cited

U.S. PATENT DOCUMENTS

| | | |
|---|---|---|
| 2013/0229622 A1 | 9/2013 | Murase et al. |
| 2013/0234930 A1 | 9/2013 | Goerger |
| 2013/0250237 A1 | 9/2013 | Ueno |
| 2013/0250242 A1 | 9/2013 | Cheng et al. |
| 2013/0301004 A1 | 11/2013 | Kahn et al. |
| 2014/0022270 A1 | 1/2014 | Rice-Jones et al. |
| 2014/0104573 A1 | 4/2014 | Iwanaga |
| 2014/0111773 A1 | 4/2014 | Itoh |
| 2014/0118693 A1 | 5/2014 | Matsuoka |
| 2014/0118697 A1 | 5/2014 | Tanaka et al. |
| 2014/0192320 A1 | 7/2014 | Tsao |
| 2014/0198298 A1 | 7/2014 | Cheng et al. |
| 2014/0204340 A1 | 7/2014 | Verdooner |
| 2014/0204341 A1 | 7/2014 | Murase |
| 2014/0211162 A1 | 7/2014 | Matsuoka et al. |
| 2014/0268046 A1 | 9/2014 | Narasimha-Iyer et al. |
| 2014/0330352 A1 | 11/2014 | Luttrull et al. |
| 2015/0002811 A1 | 1/2015 | Ota |
| 2015/0009357 A1 | 1/2015 | Seibel et al. |
| 2015/0110348 A1 | 4/2015 | Solanki et al. |
| 2015/0150449 A1 | 6/2015 | Matsumoto |
| 2015/0170360 A1 | 6/2015 | Fletcher et al. |
| 2015/0178946 A1 | 6/2015 | Krishnaswamy et al. |
| 2015/0272434 A1 | 10/2015 | Satake et al. |
| 2015/0342459 A1 | 12/2015 | Robert et al. |
| 2016/0007845 A1 | 1/2016 | Utagawa |
| 2016/0081548 A1 | 3/2016 | Wang et al. |
| 2016/0092721 A1 | 3/2016 | Kanagasingam et al. |
| 2016/0166141 A1 | 6/2016 | Kanagasingam et al. |
| 2016/0188993 A1 | 6/2016 | Beato |
| 2016/0213249 A1 | 7/2016 | Cornsweet et al. |
| 2016/0249804 A1 | 9/2016 | Wang |
| 2016/0287068 A1 | 10/2016 | Murase et al. |
| 2016/0307341 A1 | 10/2016 | Sato et al. |
| 2017/0020389 A1 | 1/2017 | Wang et al. |
| 2017/0035292 A1 | 2/2017 | Wang |
| 2017/0119241 A1 | 5/2017 | Farchione et al. |
| 2017/0161892 A1 | 6/2017 | Tellatin et al. |
| 2017/0172675 A1 | 6/2017 | Jarc et al. |
| 2017/0181625 A1 | 6/2017 | Kawakami et al. |
| 2017/0196452 A1 | 7/2017 | Wang |
| 2017/0209044 A1 | 7/2017 | Ito et al. |
| 2017/0239012 A1 | 8/2017 | Wood et al. |
| 2017/0266041 A1 | 9/2017 | Kim et al. |
| 2017/0311800 A1 | 11/2017 | Wang |
| 2017/0316565 A1 | 11/2017 | Leahy et al. |
| 2017/0332903 A1 | 11/2017 | Wang et al. |
| 2018/0092530 A1 | 4/2018 | Hart et al. |
| 2018/0249907 A1 | 9/2018 | Wang et al. |
| 2018/0263486 A1 | 9/2018 | Farchione et al. |
| 2019/0038124 A1 | 2/2019 | Wang et al. |

FOREIGN PATENT DOCUMENTS

| | | |
|---|---|---|
| CN | 102917634 A | 2/2013 |
| CN | 205006859 U | 2/2016 |
| CN | 105433899 A | 3/2016 |
| CN | 205181314 U | 4/2016 |
| EP | 2 374 404 A1 | 10/2011 |
| EP | 2425763 A1 | 7/2012 |
| GB | 2378600 A | 12/2003 |
| JP | 2006-101943 A | 4/2006 |
| JP | 2009-172157 A | 8/2009 |
| JP | 2009-219644 A | 10/2009 |
| JP | 2010-57547 A | 3/2010 |
| JP | 2011-097992 A | 5/2011 |
| JP | 2012-213575 A | 11/2012 |
| JP | 2013-46850 A | 3/2013 |
| JP | 2013-059551 A | 4/2013 |
| JP | 2013-059551 A | 4/2013 |
| KR | 10-2013-001079 A | 1/2013 |
| WO | 2004/089214 A2 | 10/2004 |
| WO | 2006016366 A2 | 2/2006 |
| WO | 2008/106802 A1 | 9/2008 |
| WO | 2010080576 A1 | 7/2010 |
| WO | 2010/115195 A1 | 10/2010 |
| WO | 2011/029064 A1 | 3/2011 |
| WO | 2012009702 A1 | 1/2012 |
| WO | 20120134272 A1 | 10/2012 |
| WO | 2013041658 A1 | 3/2013 |
| WO | 2013/082387 A1 | 6/2013 |
| WO | 2013/107464 A1 | 7/2013 |
| WO | 2014/182769 A1 | 11/2014 |
| WO | 2015/044366 A1 | 4/2015 |
| WO | 2015/170947 A1 | 11/2015 |

OTHER PUBLICATIONS

Brown et al., "Comparison of image-assisted versus traditional fundus examination," Eye and Brain, Dovepress, Feb. 2013, vol. 5, pp. 1-8.

Muller et al., "Non-Mydriatic Confocal Retinal Imaging Using a Digital Light Projector," Ophthalmic Technologies XXIII, 2013, downloaded from: http://proceedings.spiedigitallibrary.org (8 pages).

Paques et al., "Panretinal, High-Resolution Color Photography of the Mouse Fundus," Investigative Ophthalmology & Visual Science, Jun. 2007, vol. 48, No. 6, pp. 2769-2774.

Visucampro NM—The Non-Mydriatic Fundus Camera System from Carl Zeiss, Carl Zeiss Meditec, International, 2005 (1 page).

International Search Report & Written Opinion dated May 15, 2015, Application No. PCT/US2015/015124, 10pgs.

"A Portable, Scalable Retinal Imaging System," TI Engibous Competition Report (Spring 2012), Rice University, http://www.ti.com/corp/docs/university/docs/Rice_University_mobileVision%20Final%20Report.pdf, 96 pages.

Girdwain, "Goggles Differentiate Between Stroke and Vertigo," Today's Geriatric Medicine, vol. 6 No. 4 p. 8, Today's GeriatricMedicine, Oct. 1, 2013, 2 pages.

Johns Hopkins Medicine, "Small Johns Hopkins-led study finds portable device diagnoses stroke with 100 percent accuracy," www.hopkinsmedicine.org/se/util/display_mod.cfm?Module=/se-server/mod/modules/semod_printpage/mod_default.cfm&PageURL-/news/media/releases/is_i . . . , Mar. 5, 2013, 2 pages.

Dilating Eye Drops, AAPOS, http://web.archive.org/web/2012020409024/http://www.aapos.org/terms/conditions/43, Dilating Eye Drops, 2pgs, Dec. 17, 2015.

Spector, The Pupils, Clinical Methods: The History, Physical, and Laboratory Examinations, 3rd Edition, pp. 300-304, Chapter 58 (1990).

Anastasakis et al., SLO-Infrared Imaging of the Macula and its Correlation with Functional Loss and Structural changes in Patients with Stargardt Disease, May 1, 2012, 19pgs.

Carrasco-Zevallos, O. et al., "Pupil Tracking Optical Coherence Tomography for Precise Control of Pupil Entry Position," Biomedical Optics Express: 6(9): 3405-3419, Sep. 1, 2015, 15pgs.

EIDON—The First True Color Confocal Scanner on the Market, www.centervue.com, Jul. 27, 2015, 12pgs.

Grieve et al., Multi-wavelength imaging with the adaptive optics scnaning laser Ophthalmoscope, Optics Express 12230, Dec. 11, 2006, vol. 14, No. 25, 13pgs.

Hammer et al., Adaptive Optics Scanning Laser Ophthalmoscope for Stablized Retinal Imaging, Optics Express: 14 (8): 3354-3367, Apr. 17, 2006, 14pgs.

International Search Report and Written Opinion for Application No. PCT/US2015/013542 dated May 11, 2015, 12 pages.

Markow et al., "Real-Time Algorithm for Retinal Tracking," IEEE Transactions on Biomedical Engineering; 40(12): 1269-1281, Dec. 1993, 13pgs.

Moscaritolo et al., "A Machine Vision Method for Automated Alignment of Fundus Imaging Systems," Ophthalmic Surgery Lasers & Imaging: 41(6): 607-613, Sep. 29, 2010, 7pgs.

Navilas, Navigated Laser Therapy—A New Era in Retinal Disease Management, www.od-os.com, © 2015, 16pgs.

Sahin et al., "Adaptive Optics with Pupil Tracking for High Resolution Retinal Imaging," Biomedical Optics Express: 3(2): 225-239, Feb. 1, 2012, 15pgs.

(56) References Cited

OTHER PUBLICATIONS

Sheehy et al., "High-speed, Image-based eye tracking with a scanning laser ophthalmoscope," Biomedical Optics Express; 3(10): 2611-2622, Oct. 1, 2012, 12pgs.
Extended European Search Report, EP15749109.3, dated Oct. 26, 2017 (8pgs).
Land, Edwin H., "The Retinex Theory of Color Visison," Scientific America, Dec. 1977, vol. 237 No. 6 p. 108-128.
User Manual Non-Mydriatic Retinal Camera, Topcon Corporation, Tokyo, Japan, 106 pages (2014).

\* cited by examiner

FUNDUS IMAGING SYSTEM

BACKGROUND

People with type 1 or type 2 diabetes can develop eye disease as a result of having diabetes. One of the most common diabetic eye diseases is diabetic retinopathy, which is damage to the blood vessels of the light-sensitive tissue at the back of the eye, known as the retina. Eye exams can produce images of the back of the eye and trained medical professionals use those images to diagnose and treat diabetic retinopathy.

Many of the current methods used to produce the images of the back of the eye, known as a fundus, suffer from various deficiencies, often producing imperfect images that can complicate the diagnostic procedure. Traditional imaging techniques use a Bayer-patterned color filter array imaging sensor. Such techniques have low sensitivity and the resulting image often suffers demosaic artifacts caused by low color resolution. Additionally, many of the current methods require the dilation of the patient's eyes, which is uncomfortable and inconvenient.

SUMMARY

In one aspect, a non-mydriatic fundus imaging system includes: a monochrome complementary metal-oxide semiconductor image sensor array, where the sensor array comprises a plurality of pixels and is capable of global electronic shutter operations, the global shutter being capable of substantially simultaneously initiating exposure of the plurality of pixels and of a sequential readout of the photodiodes. The system also includes, in one aspect, an illumination unit operatively coupled to the image sensor array, where the illumination unit includes a light-emitting diode that can be overdriven.

In another aspect, a method for producing an image of a fundus includes: illuminating a light-emitting diode, activating a global shutter of a two-dimensional monochrome complementary metal-oxide semiconductor sensor array, where the sensor array includes a plurality of pixels that can be exposed substantially simultaneously during the global shutter activation to obtain an image of the fundus, and storing the image readout from the plurality of pixels.

Both the system and method can be used to screen for, monitor, and diagnose eye-related diseases such as diabetic retinopathy.

DETAILED DESCRIPTION

Figure 1:
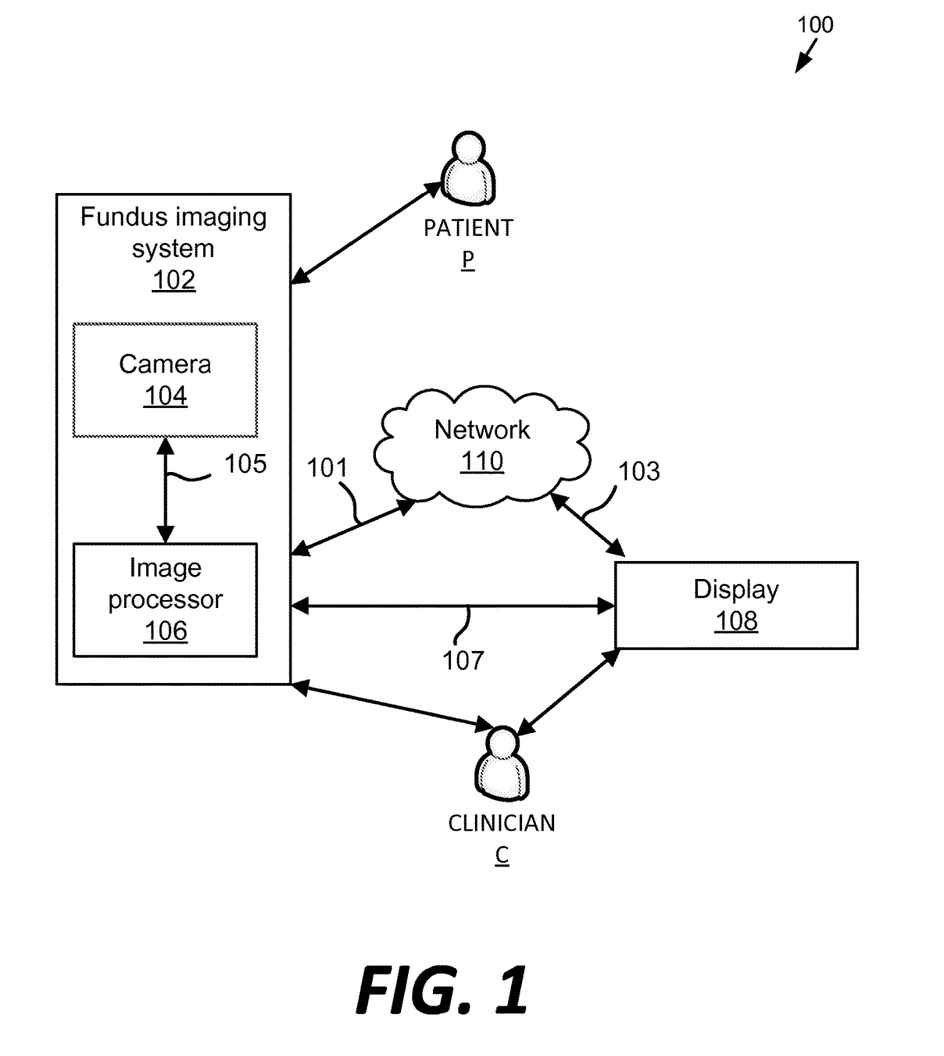
FIG. 1 illustrates one embodiment of an imaging system including a patient, a fundus imaging system, a network, a display, and a clinician.

FIG. 1 is a schematic block diagram illustrating an example system 100 for recording and viewing an image of a patient's fundus. In this example, the system 100 includes a patient P, a fundus imaging system 102, a camera 104 in communication 105 with an image processor 106, a display 108 used by clinician C with the image processor 106, and a network 110. In the example system, the fundus imaging system 102 and the display 108 are in communication either directly via communication path 107 or via the network 110 using wired and/or wireless communication schemes.

The fundus imaging system 102 functions to create a digital image of a patient's P eye fundus. As used herein, "fundus" refers to the eye fundus and includes the retina, optic nerve, macula, vitreous, choroid and posterior pole.

The patient P, in some embodiments, is being screened for an eye disease, such as diabetic retinopathy. In some embodiments, the system 102 can also be used to diagnose or monitor the progression of a disease such as diabetic retinopathy.

In some embodiments, the imaging system 102 includes a handheld housing that supports the system's components. The housing supports one or two apertures for imaging one or two eyes at a time. In some embodiments, the housing supports positional guides for the patient P, such as an adjustable chin rest. The positional guide or guides help to align the patient's P eye or eyes with the one or two apertures. In some embodiments, the housing supports means for raising and lowering the one or more apertures to align them with the patient's P eye or eyes. Once the patient's P eyes are aligned, the clinician C then initiates one or more image captures by the fundus imaging system 102.

Most known techniques for fundus imaging require mydriasis, or the dilation of the patient's pupil, which can be painful and/or inconvenient to the patient P. Example system 100 does not require a mydriatic drug to be administered to the patient P before imaging, although the system 100 can image the fundus if a mydriatic drug has been administered.

In some embodiments, the system 100 is used to assist the clinician C in screening for, monitoring, or diagnosing various eye diseases. In some embodiments, the clinician C that operates the fundus imaging system 102 is different from the clinician C evaluating the resulting image.

In the example embodiment 100, the fundus imaging system 102 includes a camera 104 in communication 105 with an image processor 106. In this embodiment, the camera 104 is a digital camera including a lens, an aperture, processor and a sensor array. The camera 104 has a sensor array equipped with a global shutter. In some embodiments, the camera 104 is configured to record an image the fundus of one eye at a time. In other embodiments, the camera 104 is configured to record an image of both eyes substantially simultaneously. In those embodiments, the fundus imaging system 102 can include two separate cameras, one for each eye.

In example system 100, the image processor 106 is operatively coupled to the camera 104 and configured to communicate with the network 110 and/or display 108. In some embodiments, the image processor 106 regulates the operation of the camera 104. An example image processor is shown in more detail in FIG. 2, which is described further below.

In some embodiments, the fundus imaging system 102 is also connected to a printer, not shown in FIG. 1. The printer can be used to produce a physical copy of the one or more fundus images produced by the fundus imaging system 102.

In example system 100, the display 108 is in communication with the fundus imaging system 102 directly 107 or via the network 110. The display 108 functions to reproduce the image produced by the fundus imaging system 102 in a size and format readable by the clinician C.

In some embodiments, the housing supports the display 108, which is embedded in the housing. In other embodiments, the display 108 is a separate component of example system 100, and may have its own housing, such as, for example, a monitor or a display on a mobile phone or tablet computer. In another embodiment, the display 108 is optional and the fundus imaging system 102 is connected to a cloud storage through network 110. In that embodiment, the fundus imaging system 102 transmits the one or more fundus images to the cloud storage and the images can be viewed by accessing the cloud storage.

A more detailed discussion of an example fundus imaging system is provided with respect to FIG. 2, below.

In one embodiment, the fundus imaging system is connected to the network 110 (connection 101). The network 110 is, in turn, connected to the display 108 (connection 103). The connections 101 and 103 may include any type of wireless network, a wired network, or any communication network known in the art. For example, wireless connections can include cellular network connections and connections made using protocols such as 802.11a, b, and/or g. In other examples, a wireless connection can be accomplished directly between the fundus imaging system 102 and the display 108 using one or more wired or wireless protocols, such as Bluetooth, Wi-Fi Direct, radio-frequency identification (RFID), or Zigbee. Other configurations are possible.

Figure 2:
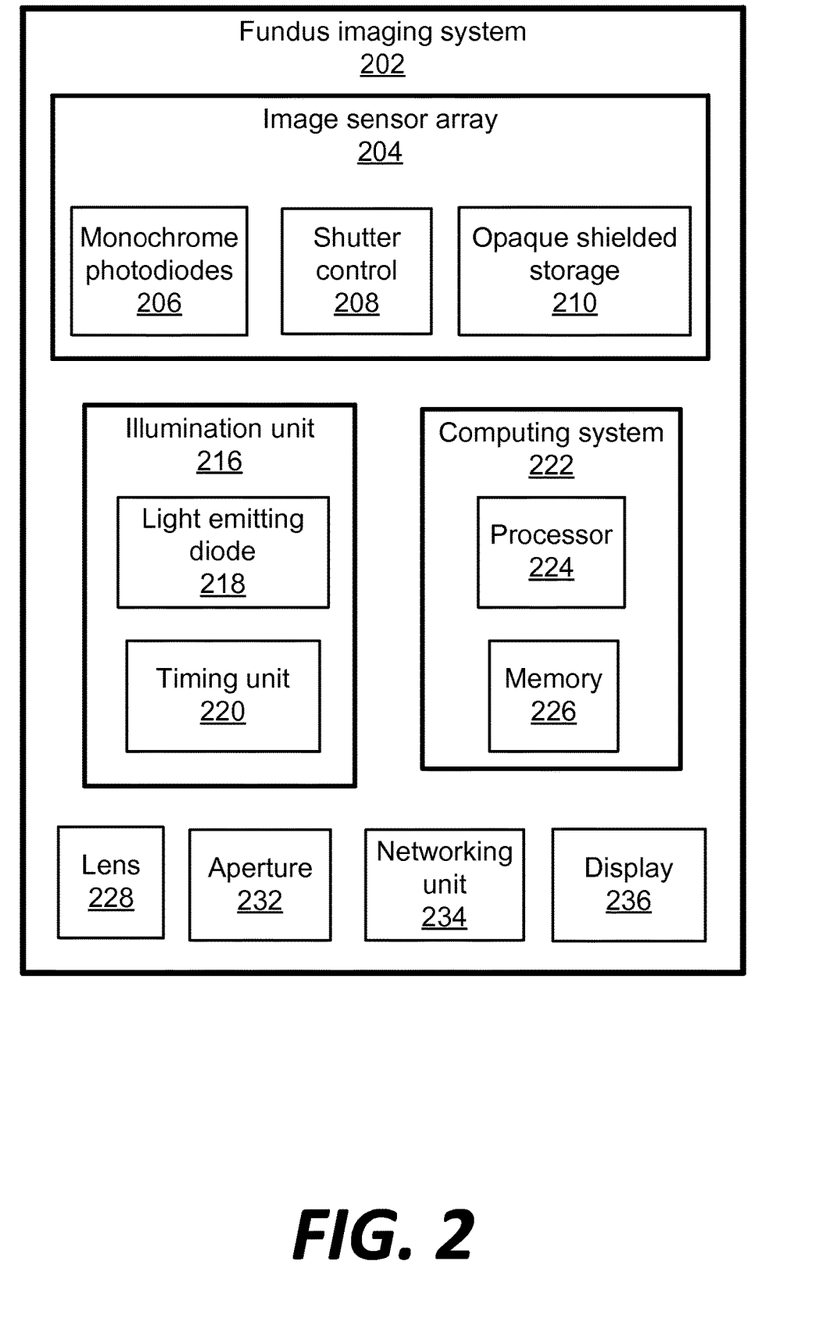
FIG. 2 illustrates a schematic diagram of an example fundus imaging system.

FIG. 2 is a block diagram of the components in an example fundus imaging system 202. The example fundus imaging system 202 includes an image sensor array 204 that comprises monochrome photodiodes 206, shutter control 208, and opaque shielded storage 210; illumination unit 216 including light-emitting diode 218 and timing unit 220; computing system 222 including processor 224 and memory 226; lens 228, an optional aperture 232, networking unit 234, and display 236.

The image sensor array 204 in the example system 202 is a complementary metal-oxide semiconductor sensor array. The example sensor array 204 includes monochrome photodiodes 206, shutter control 208, and opaque shielded storage 210. The example sensor array 204 functions to receive and process light reflected by the patient's fundus.

The image sensor array 204 has a plurality of rows of pixels and a plurality of columns of pixels. In some embodiments, the image sensor array has about 1280 by 1024 pixels, about 640 by 480 pixels, or about 1500 by 1152 pixels.

In some embodiments, the pixel size in the image sensor array 204 is from about four micrometers by about four micrometers; from about two micrometers by about two micrometers; from about six micrometers by about six micrometers; or from about one micrometer by about one micrometer.

The example monochrome photodiodes 206 have a light-receiving surface and have substantially uniform length and width. During exposure, the monochrome photodiodes 206 convert the incident light to a charge.

Shutter control 208 in example system 202 initiates the exposure of the photodiodes 206 and the end of the exposure of the photodiodes 206. In some embodiments, after the exposure period of the photodiodes 206 ends, the charge is transferred to opaque shielded storage 210. Shutter control 208 also controls the reset of the photodiodes 206 and the read-out of the stored charges to be processed by computing system 222.

Shutter control 208 is configured to operate the image sensor array 204 as a global shutter. That is, substantially all of the photodiodes are exposed simultaneously and for substantially identical lengths of time. The global exposure effectively integrates charge substantially evenly across the image sensor array 204 during the exposure time.

In another embodiment, a monochrome CMOS sensor with global reset mode can also be used without opaque shielded storage.

As discussed above with reference to FIG. 1, in some embodiments the clinician initiates the exposure of the photodiodes 206 by global reset of all the pixels. However, the shutter control 208 is configured to end the exposure period by global transferring all the pixels to their correspondent opaque shielded storages. For example, in some embodiments, shutter control 208 ends the exposure period using a predetermined time period that starts when the clinician initiates an image capture sequence. In some embodiments, an auto exposure control algorithm will determine the exposure period dynamically according to the illumination conditions and/or image contrast.

A Bayer filter, not used in example system 202, essentially blocks out two-thirds of the light incident on the image sensor array. In contrast, the monochrome photodiodes 206 used in the example system 202 do not filter out light, which in turn improves the image quality. Also, because monochrome arrays do not filter light, the example fundus imaging system 202 advantageously requires roughly one-third of the light required by a fundus imaging system that employs a Bayer filter array.

Additionally, in contrast to a system using a Bayer color filter array, the example fundus imaging system 202 can improve diabetic retinopathy screening sensitivity by reducing the number of false negatives. That is, the example fundus imaging system 202 can detect much lower contrast, and thereby detect more abnormal features, that the Bayer array cannot because the Bayer array limits the amount of imaged contrast. Additionally, the example fundus imaging system 202 can also reduce diabetic retinopathy false positives because the system 202 can produce higher uniform image quality without the Bayer array demosaic artifacts.

The illumination unit 216 in example fundus imaging system 202 provides light to illuminate the fundus and coordinate the timing with the exposure of the image sensor array. The example illumination unit includes light-emitting diode 218 and timing unit 220. Example light-emitting diode 218 is in operative communication with the computing system 222 and the timing unit 220.

Example light-emitting diode 218, in some embodiments, is a three-color light-emitting diode (LED), where the three colors are red, green, and blue. For example, the light-emitting diode 218 can be a three-channel RGB LED, where each die is capable of independent and tandem operation. In some embodiments, more than one LED 218 is used in the illumination unit 216. The LEDs have a maximum standard current draw rating of, for example, 20 mA, but the LED can be overdriven to draw more current, for example 30 mA (at 150% of maximum standard current), 200% of maximum current, 300% of maximum current, and 500% of maximum current in a low duty cycle usage. Other maximum standard current draws are possible.

In some embodiments, the one or more LEDs 218 are overdriven during the illumination period, which is controlled by timing unit 220 in example system 202. In some embodiments, the combination of overdriving the LEDs with the global shutter operation results in a shorter exposure period. The shorter exposure period, in some embodiments, results in a sharper image. Additionally, in some embodiments the shorter illumination period results in less contraction of the pupil, thereby reducing the need for pupil dilation.

In order to maintain the patient's P pupil size as large as possible without dilation, dim light must be used. In the imaging systems known in the art, this dim light requirement results in poorer image quality. For example, the image quality when a 16 ms LED illumination period is used is much better than when a 2 ms LED illumination period is used in the prior art systems. In some embodiments, the LED illumination period used in example system 202 are 2 ms, 3 ms, or 5 ms. The example fundus imaging system 202 advantageously uses a dimmer LED light and produces a higher quality image than those systems known in the art.

Each die in the LED 218 is capable of independent and tandem operation. For example, in one embodiment, three consecutive frames are captured by the image sensor array 204. The first exposure occurs when the red die is illuminated, then the second exposure occurs when the green die is illuminated, and then third exposure occurs when the blue die is illuminated. The order of die illumination is different in other embodiments.

An alternative embodiment captures three consecutive frames for the following color illuminations: red (red die on only), yellow (red and green dies on substantially simultaneously), and white (reed, green, and blue dies on substantially simultaneously). Again, the order of illumination color is different in other embodiments. In one diabetic retinopathy embodiment, the white illumination (all dies on) produces an all features detection, a red image (only red die on) assists the clinician in retinal microaneurysms and hemorrhages confirmation, and a yellow image (red and green dies on) assists the clinician in exudates confirmation.

In some embodiments, timing unit 220 activates the illumination timing of, and light emitted from, light-emitting diode 218. Timing unit 220 is, in some embodiments, a separate component including a processor and memory that is operatively coupled to the computing system 222 and image sensor array 204. In other embodiments, timing unit 220 is a computer program stored on the memory 226 and configured to be run by the processor 224.

Timing unit 220 can be configured to illuminate the light-emitting diode 218 at a time just before the image sensor array 204 initiates a global shutter exposure and to cease illumination shortly after the global shutter exposure ends. In other embodiments, the timing unit 220 can be configured to illuminate the light-emitting diode 218 after the global shutter exposure begins and to cease illumination before the global shutter exposure ends. In another embodiment, the timing unit 220 can be configured to illuminate the light-emitting diode 218 with an overlap period of time with the global shutter exposure period of time. In some embodiments the timing unit is configured to cause the light-emitting diode 218 to pulse or produce a strobe-like light during the illumination period.

In the example fundus imaging system 202, the computing system 222 includes a processor 224 communicatively connected to a memory 226 via a data bus. The processor 224 can be any of a variety of types of programmable circuits capable of executing computer-readable instructions to perform various tasks, such as mathematical and communication tasks. The memory 226 can include any of a variety of memory devices, such as using various types of computer-readable or computer storage media. A computer storage medium or computer-readable medium may be any medium that can contain or store the program for use by or in connection with the instruction execution system, apparatus, or device. In the context of the present disclosure, a computer storage medium includes at least some tangible component, i.e., is not entirely consisting of transient or transitory signals The example system 202 also includes a lens 228 supported by the housing. Some embodiments have more than one lens supported by the housing. For example, one lens is used to focus the light incident on the image sensor array 204 and another lens to focuses the light from the illumination unit 216. Some embodiments use more than one lens to focus the incident light. In some embodiments, the lens has mechanical power and control connections coupled to the computing system 222. The computing system 222 may be configured to control the position of the lens or lenses to optimize lens positioning for auto focusing for the image sensor array 204 and illumination unit 216. In some embodiments, lens focusing is required in spite of a standard positioning guide for the patient because of unique facial geometries.

The example fundus imaging system 202 has, optionally, one or more apertures 232 supported by the housing. In some embodiments, the aperture 232 is an annular piece that supports a lens 228. The patient's eye is aligned substantially with the aperture 232 before the fundus is imaged. In some embodiments, the aperture is a mechanically operated cover that can be opened and closed based upon signals from the computing system 222.

In some embodiments, the example fundus imaging system 202 has a display 236 for the clinician to focus and examine the patient's eye fundus.

In some embodiments, the imaging system 202 has a networking unit 234. Networking unit operates to enable communication between the fundus imaging system 202 and the example display 108 or other networked devices. The networking unit 234 may be in wireless or wired communication with the display 108 or other networked devices.

Additionally, the networking unit 234 is in communication with the network 110. In some embodiments, the networking unit 234 communicates with the display 108 over a wired or wireless connection.

In some embodiments, the fundus imaging system 202 also includes an anti-aliasing filter, not pictured in FIG. 2. The optional anti-aliasing filter is in some embodiments an optical low-pass filter. This filter is a thin layer located between the monochrome photodiodes 206 and the direction from which the incident light emanates. The filter, in some embodiments, prevents the occurrence of a pattern (moiré or other artifacts) different from the original image.

In some embodiments, the fundus imaging system 202 also includes reflective mirrors, not shown in FIG. 2. The optional one or more reflective mirrors are used to direct light to the image sensor array 204 and from the illumination unit 216. In some embodiments, the one or more mirrors are supported by, and fixed to, the housing. In other embodiments, the reflective mirror or mirrors are supported by the housing but have adjustable positions, where the clinician or computing system 222 can adjust the positioning of the mirrors. The example system is operable without reflective mirrors.

Figure 3:
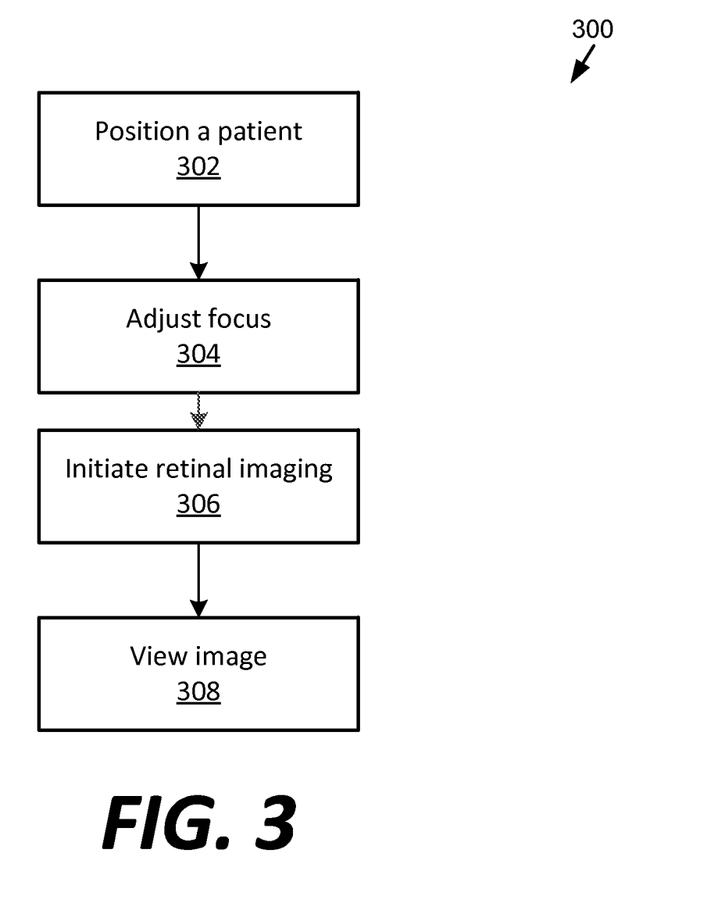
FIG. 3 illustrates a flowchart of an example use by a clinician of the example fundus imaging system.

FIG. 3 is a block flow diagram of an example use 300 by a clinician of the example fundus imaging system. Example use 300 is performed in some embodiments by more than one clinician. Example use 300 includes positioning a patient 302, adjusting the focus 304, initiating a retinal imaging 306, and viewing the image 308 created by the scan. Other embodiments may omit steps or include additional steps.

Example use 300 begins when the clinician positions a patient 302. The patient may be seated or standing. Positioning 302 includes aligning the patient such that one or more of the patient's eyes are aligned with the aperture or apertures of the fundus imaging system. In some embodiments, the display coupled to the imaging system shows a preview image to help guide the clinician in positioning the patient. In some embodiments, the system emits an audible sound to notify the clinician that the patient's eye is in a proper position.

In some embodiments, there is a positioning structure, such as a chin rest or head support structure, to assist in positioning the patient. In some embodiments, the positioning structure has means for adjustment that can be used by the clinician in positioning the patient's eye relative to the housing. In other embodiments, the positioning structure is fixed and the housing has adjustment means such that the clinician can reposition the housing to be in alignment with the patient's eye or eyes.

After the patient is positioned, the next step in example use 300 is for the clinician to adjust the focus 304 on the fundus imaging system. In some embodiments, the fundus imaging system has one or more adjustable foci. These foci may be manually adjusted by the clinician, electronically adjusted by the clinician, or automatically adjusted by the fundus imaging system. In some embodiments, the focus adjusts the position of the lens through which the incident light passes. In some embodiments, the focus adjusts the lens through which the light from the illumination unit passes. In some embodiments, the clinician initiates the automatic focusing by the fundus imaging system by pressing a button or selecting an icon on a graphical user interface. In some embodiments, the adjust focus step 304 can be replaced by auto focusing algorithms without human intervention.

Figure 4:
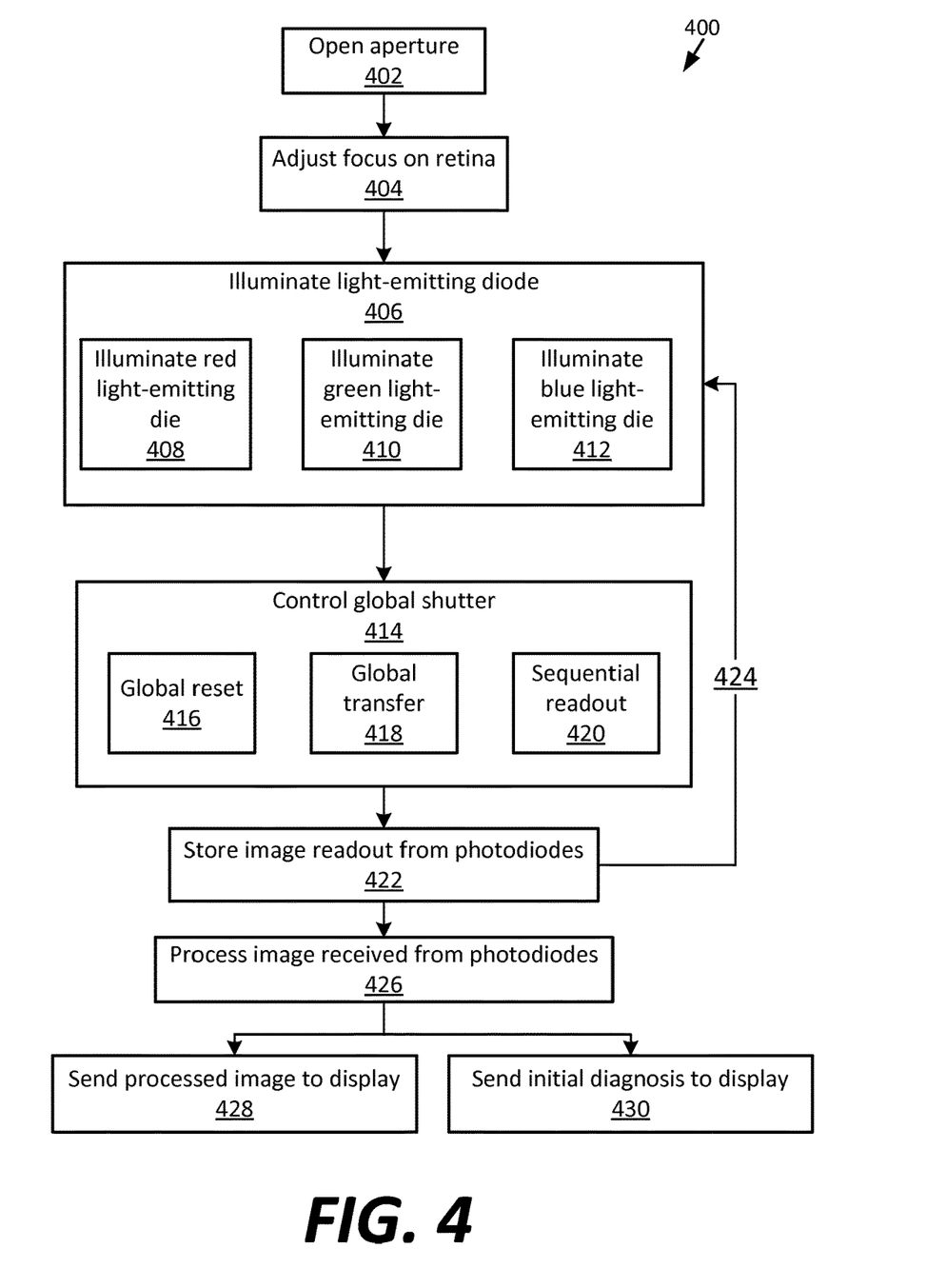
FIG. 4 illustrates a flowchart of an example method of operation of the example fundus imaging system.

Next, the clinician initiates the retinal imaging 306 in example use 300. In some embodiments, the clinician initiates the retinal imaging 306 by pressing a button or selecting an icon on a graphical user interface. An example of the fundus imaging system's steps during retinal imaging 306 is shown in FIG. 4 and described in detail below. In some embodiments, the clinician may return to step 302 to reposition the patient's other eye for imaging and repeat steps 304 and 306. In other embodiments, the clinician may view the image 308, and may ensure that the image is of acceptable quality, before returning to step 302 to image the patient's other eye.

Additionally, in some embodiments, initiate retinal imaging 306 is replaced by passive eye tracking algorithms to automatically trigger the image capture without human intervention. Passive eye tracking is described with reference to FIG. 5 below.

After the fundus imaging system images the retina 306, the clinician views the fundus image 308 in example use 300. If any image is not satisfactory to the clinician, the clinician may repeat example use 300. Examples of the types of displays that may be used in step 308 are described in more detail with reference to block 108 in FIG. 1.

FIG. 4 illustrates a block flow diagram of an example method of operation 400 of the fundus imaging system. Example operation 400 includes the fundus imaging system performing the steps of open aperture 402, adjust focus on retina 404, illuminate light-emitting diode 406, which includes illuminate red light-emitting die 408, illuminate green light-emitting die 410, and illuminate blue light-emitting die 412, control global shutter 414, which includes global reset 416, global transfer 418, sequential readout of photodiodes 420, store image read from photodiodes 422, optionally returning to the illuminate light-emitting diode step 406, process image read from photodiodes 426, send processed image to display 428, and send initial diagnosis to display 430. Alternate embodiments may have fewer or additional steps, or perform the steps in a different order.

In example operation 400, the first step is to, optionally, open aperture 402. As described above with reference to aperture 232, in some embodiments the aperture can be a cover opened and closed through electrical or mechanical means. In some embodiments, the aperture is a frame that, in some embodiments, supports a lens but does not have an operable cover. One purpose of the open aperture step 402 is to enable incident light to pass through one or more lenses towards the image sensor array.

Adjust focus on the retina 404 is the next step in example operation 400. In some embodiments, the clinician operating the fundus imaging system manually changes one or more focal lengths. Adjusting the focus can be accomplished by, for example, mechanical means such as a knob or knobs or through electrical means such as a graphical user interface displaying focus adjustment parameters, where the interface is operatively coupled to adjustment means that is coupled to the one or more lenses. Adjusting the focus can also be accomplished automatically by auto focusing algorithms controlling a mechanical means without human intervention.

The next step in example operation 400 is to illuminate the light-emitting diode 406. The illuminate light-emitting diode step 406 comprises illuminating one or more of the colored dies in the red-green-blue light-emitting diode: illuminate the red die in the diode 408, illuminate the green die in the diode 410, and illuminate the blue die in the light-emitting diode 412. Other combinations of colors are possible, including, for example, cyan-magenta-yellow, red-green only or white-red only.

As discussed above, some embodiments of the imaging system have more than one light-emitting diode. Additionally, in some embodiments of operation 400, the illuminate step 406 occurs either after or concurrently with the global reset step 416. The illuminate step 406 is performed multiple times, consecutively, in some embodiments.

As discussed above, in some embodiments, one image is taken with all three dies illuminated 408, 410, and 412, producing white light. In some embodiments, the system initiates four consecutive image captures. In those embodiments, the illumination unit is configured to produce white light for the first image capture, then red, green, and blue for the subsequent image captures. Other sequences in other embodiments are described in more detail with reference to illumination unit 216 in FIG. 2.

The light-emitting diodes are illuminated 406 for a short period of time. In some embodiments, the diode, or diodes, are illuminated for less than 5 milliseconds, for less than 2 milliseconds, for less than 1 millisecond, or for less than 0.5 milliseconds. As discussed above, the light-emitting diode may be overdriven for some or all illuminations. One of many advantages of the example embodiments is that the intensity, or the period, of the light-emitting diodes can be reduced by from about 5 to about 200 times those imaging systems in the art using a rolling shutter/reset CMOS sensor.

Control global shutter step 414 includes the global reset step 416, the global transfer step 418, and sequential readout step 420. The computing system, operatively coupled to the image sensor array, controls the image sensor array's global shutter in example operation 400.

Global reset step 416 involves, in some embodiments, resetting and exposing every pixel in the image sensor array substantially simultaneously. The exposure of the pixels is as short as possible to avoid motion blur and to limit the amount of time the patient's pupils must be illuminated. In some embodiments the exposure time is about 2 milliseconds.

Global transfer step 418 involves, in some embodiments, simultaneously ceasing the exposure of every pixel in the image sensor array and transferring the charge from each pixel into the opaque shielded storage. An example global shutter is described in more detail with reference to image sensor array 204 in FIG. 2, above.

Sequential readout step 420 in example operation 400 involves each pixel in the image sensor array being readout sequentially (one pixel after the other). The readout step 420 is accomplished, in some embodiments, by the computing system sending a readout clocking signal to the image sensor array to read out pixel value one by one.

After the global transfer step 418, the pixel exposure is ended in example operation 400 and the image readout from the photodiodes' opaque shielded storage unit is stored 422 in memory. In some embodiments, multiple images are captured consecutively and the example operation repeats 424. Return step 424 is shown in FIG. 4 as returning to step 406, but in other embodiments the return step 424 begins by opening the aperture 402 or by adjusting the focus on the retina 404 step.

Next, the processor processes the image readout from the photodiodes' opaque shielded storage 426 in example operation 400. In some embodiments, processing of the image is performed in accordance with a software program stored on the memory and run in the processor.

In some embodiments, processing 426 includes amplifying the data generated from the incident light and converting the generated data into a digital signal. Processing 426 may also include storing a set of digital signal values corresponding to incident light on the plurality of pixels of image sensor array as a frame of image data. In some embodiments, the process image step 426 does not use color demosaic algorithms.

Process image step 426 includes a processor running image processing algorithms to, for example, perform image enhancement, perform features detection, and identify a classification to correct the diabetic retinopathy.

For example, the algorithm can access an evaluation database for diabetic retinopathy such as DIARETDB0 and DIARETDB1, established by Lappeenrata University of Technology and University of Kuopio Medical Faculty in Finland. Those databases consist of about 219 fundus images that have been evaluated and annotated by experts and doctors to establish diagnosis results for those images. An example output of an evaluation algorithm, when using a fundus image as an input, is that small red dots exist, there are hemorrhages and hard exudates are detected in the fundus. The output can identify both a list of the diagnoses and the number of observed issues. In some embodiments, the output can also identify the detected issues on the fundus image, using, for example, graphics such as circles or arrows.

In some embodiments, the clinician can select the one or more issues the algorithm running on the processor should identify during processing step 426. For example, in one embodiment the clinician selects through a graphical user interface "hemorrhages" in a menu containing possible diabetic retinopathy symptoms. The processed image then will contain identifying indicia such as on-screen arrows, circles or other identifying icons. Thus, where applicable, the image in this embodiment contains indicia flagging detected hemorrhages. But because, in this example, the clinician did not select any other symptoms, such as "exudates", even if present, the image will not contain indicia flagging other symptoms.

In an alternate embodiment, the processor is configured to detect all possible symptoms and the image contains indicia flagging all detected symptoms. Then, in some embodiments, the clinician uses a menu-type filter to select one or more symptoms to be flagged on the display.

In another embodiment, the image stored from the photodiode readout is sent to a remote cloud storage and further processed, using algorithms described above, in a remote server.

In example operation 400, the computing system sends the processed image to the display 428 and/or sends an initial diagnosis to display 430. As discussed above, in some embodiments, the system produces a raw image that does not contain any diagnostic identification information 428. In other embodiments, the system produces an image accompanied by diagnostic information 430.

Figure 5:
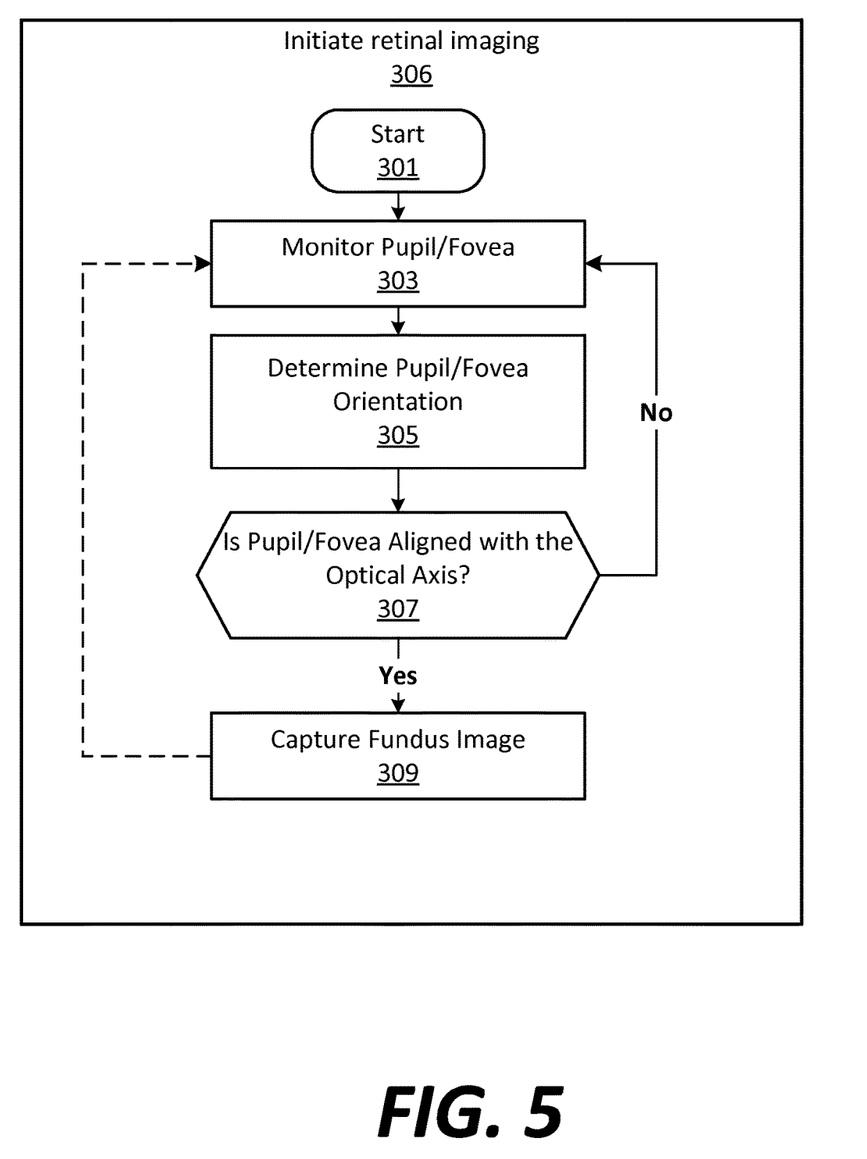
FIG. 5 illustrates an example method of initiating a fundus imaging using passive eye tracking.

FIG. 5 illustrates an alternate embodiment of initiate retinal imaging step 306 using passive eye tracking. The initiate retinal imaging step 306 operates to image the fundus of the patient P using passive eye tracking. In the initiate retinal imaging step 306, the fundus imaging system 202 monitors the pupil/fovea orientation of the patient P. Although the initiate retinal imaging step 306 is described with respect to fundus imaging system 202, the initiate retinal imaging step 306 may be performed using a wearable or nonwearable fundus imaging system, such as a handheld digital fundus imaging system.

Initially, at step 303, the pupil or fovea or both of the patient P are monitored. The fundus imaging system 202 captures images in a first image capture mode. In the first image capture mode, the fundus imaging system 202 captures images at a higher frame rate. In some embodiments, in the first image capture mode, the fundus imaging system 202 captures images with lower illumination and at lower resolutions. In some embodiments, the lower illumination is created by the illumination unit 216 operating to generate and direct light of a lower intensity towards the subject. In other embodiments, the lower illumination is created by an external light source or ambient light. The first image capture mode may minimize discomfort to the patient P, allow the patient P to relax, and allow for a larger pupil size without dilation (non-mydriatic).

Next, at step 305, the computing system 222 processes at least a portion of the images captured by the fundus imaging system 202. The computing system 222 processes the images to identify the location of the pupil or fovea or both of the patient P. Using the location of the pupil or fovea or both in one of the images, a vector corresponding to the pupil/fovea orientation is calculated. In some embodiments, the pupil/fovea orientation is approximated based on the distance between the pupil and fovea in the image. In other embodiments, the pupil/fovea orientation is calculated by approximating the position of the fovea relative to the pupil in three dimensions using estimates of the distance to the pupil and the distance between the pupil and the fovea. In other embodiments, the pupil/fovea orientation is approximated from the position of the pupil alone. In yet other embodiments, other methods of approximating the pupil/fovea orientation are used.

Next, at step 307, the pupil/fovea orientation is compared to the optical axis of the fundus imaging system 202. If the pupil/fovea orientation is substantially aligned with the optical axis of the fundus imaging system 202, the process proceeds to step 309 to capture a fundus image. If not, the process returns to step 303 to continue to monitor the pupil or fovea. In some embodiments, the pupil/fovea orientation is substantially aligned with the optical axis when the angle between them is less than two to fifteen degrees.

Next, at step 309, a fundus image is captured. In some embodiments, the fundus image is captured in a second image capture mode. In some embodiments, in the second image capture mode, the fundus imaging system 202 captures images with higher illumination and at higher resolutions. In some embodiments, the higher illumination is created by the illumination unit 216 operating to generate and direct light of a higher intensity towards the subject. In other embodiments, the higher illumination is created by an external light source or ambient light. The second image capture mode may facilitate capturing a clear, well-illuminated, and detailed fundus image.

In some embodiments, after step 309, the initiate retinal imaging step 306 returns to step 303 to continue to monitor the pupil/fovea orientation. The initiate retinal imaging step 306 may continue to collect fundus images indefinitely or until a specified number of images have been collected. Further information regarding passive eye tracking can be found in U.S. patent application Ser. No. 14/177,594, titled Ophthalmoscope Device, filed on even date herewith, which is hereby incorporated by reference in its entirety.

The flow diagrams depicted herein are just examples. There may be many variations to these diagrams or the steps (or operations) described therein without departing from the spirit of the disclosure. For instance, the steps may be performed in a differing order, or steps may be added, deleted or modified.

While embodiments have been described, it will be understood that those skilled in the art, both now and in the future, may make various improvements and enhancements can be made.

The invention claimed is:

1. A non-mydriatic fundus imaging system, comprising:
   an image sensor array capable of global reset operations, the global reset operations including exposing each pixel of a plurality of rows of pixels substantially simultaneously;
   an illumination unit operatively coupled to the image sensor array, wherein the illumination unit includes a multi-die light emitting diode;
   a timing unit operatively coupled to the image sensor array and the illumination unit and configured to simultaneously expose each pixel of the plurality of rows of pixels of the image sensor array during an exposure period;
   a processor; and
   memory storing instructions that, when executed by the processor, cause the non-mydriatic fundus imaging system to:
      capture a plurality of images in a first image capture mode;
      process at least a portion of the plurality of images to determine a position of a pupil of a subject; and
      capture an image in a second image capture mode when the position of the pupil is substantially aligned with an optical axis of the non-mydriatic fundus imaging system;
      wherein the first image capture mode comprises a first resolution and a first illumination condition;
      wherein the second image capture mode comprises a second resolution and a second illumination condition;
      wherein the second resolution is greater than or equal to the first resolution; and
      wherein the second illumination condition is brighter than the first illumination condition.

2. The non-mydriatic fundus imaging system according to claim 1, the image sensor array including a two-dimensional monochrome complementary metal-oxide-semiconductor.

3. The non-mydriatic fundus imaging system according to claim 1, the second image capture mode including overdrive of the multi-die light emitting diode during the global reset operations.

4. The non-mydriatic fundus imaging system according to claim 3, the illumination unit being configured to emit monochrome light for less than 2 milliseconds during the second image capture mode.

5. The non-mydriatic fundus imaging system according to claim 4, the illumination unit being configured to cause the multi-die light emitting diode to, consecutively, illuminate red light only, illuminate green light only, and illuminate blue light only.

6. The non-mydriatic fundus imaging system according to claim 4, the illumination unit being configured to cause the multi-die light emitting diode to illuminate red, green and blue simultaneously.

7. The non-mydriatic fundus imaging system according to claim 1, the image sensor array further being capable of global transfer operations, the global transfer operations including simultaneously ceasing exposure of each pixel in the image sensor array.

8. The non-mydriatic fundus imaging system according to claim 7, the global transfer operations further including transferring charge from each pixel in the image sensor array into opaque shielded storage.

9. The non-mydriatic fundus imaging system according to claim 8, the image sensor array further being capable of sequential readout operations.

10. A method for producing an image of a fundus, the method comprising:
    illuminating a light emitting diode, the light emitting diode being a multi-color die LED, wherein illuminating the light emitting diode includes emitting monochrome light for less than 2 milliseconds;
    activating a shutter of an image sensor array capable of exposing each pixel of a plurality of rows of pixels substantially simultaneously; and
    storing an image readout from the plurality of rows of pixels.

11. The method according to claim 10, further comprising initiating global transfer operations, including simultaneously ceasing exposure of each pixel in the image sensor array.

12. The method according to claim 11, the initiating global transfer operations further including transferring charge from each pixel in the image sensor array into opaque shielded storage.

13. The method according to claim 11, further comprising initiating sequential readout operations.

14. The method according to claim 10, wherein illuminating the light emitting diode includes illuminating red light only, illuminating green light only, and illuminating blue light only; and
    further comprising capturing an image during each of illuminating red light only, illuminating green light only, and illuminating blue light only.

15. A non-mydriatic fundus imaging system, comprising:
an image sensor array, configured for:
- global reset operations, the global reset operations including exposing each pixel of a plurality of rows of pixels substantially simultaneously,
- global transfer operations, the global transfer operations including simultaneously ceasing exposure of each pixel in the image sensor array and transferring charge from each pixel in the image sensor array into opaque shielded storage; and
- sequential readout operations;

an illumination unit operatively coupled to the image sensor array, the illumination unit including a multi-die light emitting diode;

a timing unit operatively coupled to the image sensor array and the illumination unit and configured to simultaneously expose a full frame of pixels of the image sensor array during an exposure period;

a processor; and memory storing instructions that, when executed by the processor, cause the non-mydriatic fundus imaging system to:
- capture a plurality of images in a first image capture mode;
- process at least a portion of the plurality of images to determine a position of a pupil of a subject;
- capture an image in a second image capture mode when the position of the pupil is substantially aligned with an optical axis of the non-mydriatic fundus imaging system, the first image capture mode comprises a first resolution and a first illumination condition;

the second image capture mode comprises a second resolution and a second illumination condition;

the second resolution is greater than or equal to the first resolution; and the second illumination condition is brighter than the first illumination condition the image sensor array including a two-dimensional monochrome complementary metal-oxide-semiconductor; and the illumination unit being configured to emit monochrome light for less than 2 milliseconds during the second image capture mode.

* * * * *